US00PP16357P3

(12) United States Plant Patent
Miyazaki

(10) Patent No.: US PP16,357 P3
(45) Date of Patent: Mar. 21, 2006

(54) *SENECIO* PLANT NAMED 'SUSENERABU'

(50) Latin Name: ***Senecio cruentus*×*Senecio heritieri***
Varietal Denomination: Sunsenerabu

(75) Inventor: Kiyoshi Miyazaki, Hikone (JP)

(73) Assignee: Suntory Flowers Limited, Tokyo (JP)

( * ) Notice: Subject to any disclaimer, the term of this patent is extended or adjusted under 35 U.S.C. 154(b) by 92 days.

(21) Appl. No.: 10/611,353

(22) Filed: Jun. 30, 2003

(65) Prior Publication Data

US 2004/0268453 P1 Dec. 30, 2004

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,104 P2 9/2001 Miyazaki
PP12,122 P2 10/2001 Miyazaki
PP12,162 P2 10/2001 Miyazaki
PP12,181 P2 10/2001 Miyazaki

FOREIGN PATENT DOCUMENTS

JP PBR 10653 9/2002

OTHER PUBLICATIONS

Japanese Laid Open Application #12095 of JP PBR 10653, Aug. 4, 2000, Miyazaki.

*Primary Examiner*—Kent Bell
*Assistant Examiner*—Louanne Krawczewicz Myers
(74) *Attorney, Agent, or Firm*—Christie, Parker and Hale, LLP

(57) ABSTRACT

Disclosed herein is a *Senecio* plant named 'Sunsenerabu', which is tall and dome-shaped with abundant branching. Petiole length is longer than *Senecio* L. It has a large inflorescence cluster. Capitula is a single inflorescence with small obscure marginal variegation. The color of the ray florets is light violet and the color of the disc florets is strong violet. Blooming term is longer than *Senecio cruentus*. Flower buds grow one after another from the axil.

2 Drawing Sheets

Botanical classification: *Senecio cruentus*×*Senecio heritieri.*
Varietal denomination: cv. 'Sunsenerabu'.

BACKGROUND OF THE INVENTION

The present invention relates to a new and distinct variety of *Senecio* plant named 'Sunsenerabu'. 'Sunsenerabu' is a distinct and unique variety, a dome-shaped plant with abundant branching, light violet inflorescences, and a long blooming term.

There are many varieties of *Senecio cruentus* cultivated in the world, including varieties with inflorescences of a single color of white, pink, red, blue or violet. Some varieties have marginal variegation with off color parts.

The female parent used in the crossing of 'Sunsenerabu' is a clone of our own breeding line, *Senecio cruentus,* '8S-84e' (not patented in the United States), which is a compact, dome-shaped plant, approximately 16 cm in height. The stems are thick, approximately 8.0 mm in diameter, with no anthocyanin coloration. The leaf is in a serrated heart form with moderate yellow green coloration. The leaf size is medium, approximately 12.0 cm long, and approximately 12.5 cm wide. The capitulum is single flowered and has white ray florets with white disc florets having no marginal variegation. '8S-84e' has some scent.

The pollen parent used in the crossing of 'Sunsenerabu' is our breeding line, *Senecio heritieri* (an unnamed plant; not patented or sold in the United States), which was first introduced from England. *Senecio heritieri* is a high, dome-shaped point, approximately 26 cm in height with abundant branching. Stems are approximately 5.1 mm in diameter, with no anthocyanin coloration. The leaf is in a serrated heart form and light yellowish green in coloration. The leaf size is small, approximately 5.5 cm long and approximately 6.3 cm wide. The capitulum is single flowered, having strong purple ray florets with vague white parts and strong reddish purple disc florets. *Senecio heritieri* has no scent.

The controlled crossing of a plant of *Senecio cruentus* '8S-84e' and a plant of *Senecio heritieri* (unnamed) was conducted in Omori-cho, Yokaichi-shi, Shiga, Japan in February, 1999. Seedlings from this crossing have been grown since September, 1999. Four strains were selected in January 2000 in view of flower color and earliness of bloom. After multiplication by tissue culture, the botanical characteristics of the selected new strains were tested in pots starting in September 2000, using the varieties 'Sunsenebu' (U.S. Plant Pat. No. 12,104, issued Sep. 25, 2001), and 'Miss Yokohama' (not patented in the United States) for comparison.

One seedling was propagated by a cutting in Yokaich-shi, Shiga-ken, Japan. The new variety reproduces true to type in successive generations of asexual reproduction. This new variety of *Senecio* plant was named 'Sunsenerabu' (*Senecio cruentus*×*Senecio heritieri*).

The parent plants, *Senecio cruentus,* '8S-84e', and *Senecio heritieri* (unnamed), are presently maintained at Shiga-ken, Japan.

In the following descriptions, the color-coding is in accordance with the Horticultural Colour Chart of The Royal Horticultural Society, London, England (R.H.S.).

The botanical characteristics of the female parent plant *Senecio cruentus,* '8-S84e', used in the crossing of 'Sunsenerabu' are as follows.

Plant:
*Growth habit.*—Dwarf compact.
*Height.*—Approximately 16 cm.
Stem:
*Thickness.*—Approximately 8.0 mm.
*Color.*—Moderate yellowish green (Near R.H.S. 139C).
*Anthocyanin coloration.*—Absent.
*Branching.*—Fair.
*Pubescence.*—Sparse.
*Internode length at the middle of main stem.*—Approximately 0.5 cm.
Leaf:
*Whole shape.*—Heart form with a swollen basal part, which is notched where the basal part of the blade attaches to the petiole.
*Depth of concavity of leaf margin.*—Medium.
*Type of convexity.*—Acute.
*Apex shape.*—Obtuse.
*Base shape.*—Cordate.
*Degree of undulation.*—Fair.
*Length.*—Approximately 12.0 cm.
*Width.*—Approximately 12.5 cm.
*Diameter of petiole.*—Approximately 5.0 mm.
*Length of petiole.*—Approximately 5.5 cm.
*Color of upper surface.*—Moderate yellow green (Near R.H.S. 137C).
*Color of reverse surface.*—Grayish yellow green (Near R.H.S. 138B).
*Anthocyanin coloration of reverse surface.*—Absent.
*Pubescence of upper surface.*—Present.
*Pubescence of reverse surface.*—Dense.
*Color of pubescence of reverse surface.*—White.
Flower cluster (gathering of corymbs):
*Shape of flower cluster:*—Flat.
*Diameter of flower cluster.*—Approximately 20 cm.
*Height of flower cluster.*—Approximately 8 cm.
Capitula:
*Transected shape of capitula.*—Flat.
*Diameter of capitula.*—Approximately 5.5 cm.
*Diameter of entire disc.*—Approximately 1.2 cm.
*Color of ray florets.*—White (Near R.H.S. 155D).
*Marginal variegation.*—Absent.
*Color of disc florets.*—White (Near R.H.S. 155D).
*Ray floret length.*—Approximately 2.1 cm.
*Ray floret width.*—Approximately 1.0 cm.
*Shape of ray florets.*—Elliptical.
*Lengthwise warp of ray florets.*—Flat.
*Concavity of ray florets tip.*—Present.
*Shape of ray floret tip.*—Rounded.
*Number of ray florets.*—Approximately 13.
*Number of disc florets.*—Approximately 105.
*Diameter of pedicel of the first capitulum.*—Approximately 1.6 mm.
*Length of pedicel of the first capitulum.*—Approximately 2.4 cm.
*Number of capitula per flower cluster.*—Approximately 75.
*Scent.*—Present.
Phyllaries:
*Length.*—Approximately 2.2 mm.
*Color.*—Moderate yellow green (Near R.H.S. 139C).
*Anthocyanin coloration.*—Absent.
Pistil:
*Color.*—Light yellow (Near R.H.S. 11B).
*Number.*—1.
*Type.*—Style branches truncate (i.e., the top of the style is separated into two and the shape of the top is truncated.
Stamen:
*Color.*—Brilliant yellow (Near R.H.S. 12B).
*Type.*—5 anthers are connate, with separated filaments.
Blooming period — January (Sowing in August).
Hardiness:
*Cold.*—Good.
*Rain.*—Good.
*Heat.*—Good.
Resistance:
*Disease.*—Good.
*Insect.*—Good.

The botanical characteristics of the male parent plant *Senecio heritieri* used in the crossing of 'Sunsenerabu' are as follows.

Plant:
*Growth habit.*—Dwarf compact.
*Height.*—Approximately 26 cm.
Stem:
*Thickness.*—Approximately 5.1 mm.
*Color.*—Very pale green (Near R.H.S. 128D).
*Anthocyanin coloration.*—Absent.
*Branching.*—Abundunt.
*Type of primary lateral shoot.*—Branch from every node.
*Pubescence.*—Dense.
*Internode length at the middle of main stem.*—Approximately 0.8 cm.
Leaf:
*Whole shape.*—Heart form with a swollen basal part, which is notched where the basal part of the blade attaches to the petiole.
*Depth of concavity of leaf margin.*—Medium.
*Type of convexity.*—Acute.
*Apex shape.*—Obtuse.
*Base shape.*—Cordate.
*Degree of undulation.*—Weak.
*Length.*—Approximately 5.5 cm.
*Width.*—Approximately 6.3 cm.
*Diameter of petiole.*—Approximately 4.2 mm.
*Length of petiole.*—Approximately 7.5 cm.
*Color of upper surface.*—Lightly yellowish green (near R.H.S. 136D).
*Color of reverse surface.*—Very pale green (near R.H.S.128D).
*Anthocyanin coloration of reverse surface.*—Absent.
*Pubescence of upper surface.*—Dense.
*Pubescence of reverse surface.*—Dense.
*Color of pubescence of reverse surface.*—White.
Flower cluster (gathering of corymbs):
*Shape of flower cluster.*—Uneven.
*Diameter of flower cluster.*—Approximately 18 cm.
*Height of flower cluster.*—Approximately 15 cm.

Capitula:
*Transected shape of capitula.*—Flat.
*Diameter of capitula.*—Approximately 4.8 cm.
*Diameter of entire disc.*—Approximately 0.9 cm.
*Color of ray florets.*—Strong purple (near R.H.S.81B).
*Marginal variegation.*—Present.
*Diameter of off color part.*—Approximately 1.3 cm.
*Border of marginal variegation.*—Vague.
*Color of disc florets.*—Strong reddish purple (Near R.H.S. No.72A).
*Ray floret length.*—Approximately 2.2 cm.
*Ray floret width.*—Approximately 0.4 cm.
*Shape of ray florets.*—Rectangular.
*Lengthwise warp of ray florets.*—Flat.
*Concavity of ray floret tip.*—Present.
*Shape of ray floret tip.*—Acute.
*Number of ray florets.*—Approximately 13.
*Number of disc florets.*—Approximately 110.
*Diameter of pedicel of the first capitulum.*—Approximately 1.2 mm.
*Length of pedicel of the first capitulum.*—Approximately 2.5 cm.
*Number of capitula per plant.*—Approximately 35.
*Scent.*—Absent.
Phyllaries:
*Length.*—Approximately 3.1 mm.
*Color.*—Very pale green (Near R.H.S. 128D).
*Anthocyanin coloration.*—Present.
Pistil:
*Color.*—Strong reddish purple (Near R.H.S. 72A).
*Number.*—1.
*Type.*—Style branches truncate (i.e., the top of the style is separated into two and the shape of the top is truncated).
Stamen:
*Color.*—Strong reddish purple (Near R.H.S. 72A).
*Type.*—5 anthers are connate, with separated filaments.
Blooming period — End of January (Sowing in August).
Hardiness:
*Cold.*—Good.
*Rain.*—Good.
*Heat.*—Good.
Resistance:
*Disease.*—Good.
*Insect.*—Good.

The botanical characteristics of similar variety 'Sunsenebu' (*Senecio cruentus*×*Senecio heritieri*), used as a comparison variety, are as follows.

Plant:
*Growth habit.*—Semi-erect.
*Height.*—Approximately 33 cm.
Stem:
*Thickness.*—Approximately 4.5 mm.
*Color.*—Very pale green (Near R.H.S. 147C).
*Anthocyanin coloration.*—Present; uneven.
*Degree of anthocyanin coloration.*—Light.
*Branching.*—Abundant, i.e., approximately 9 to 11 branches.
*Type of primary lateral shoot.*—Branch from every node.
*Pubescence.*—Sparse.
*Internode length at the middle of main stem.*—Approximately 1.4 cm.
Leaf:
*Whole shape.*—Heart form with a swollen basal part, which is notched where the leaf attaches to the petiole.
*Depth of concavity of leaf margin.*—Approximately 7 mm on average.
*Type of convexity.*—Acute.
*Apex shape.*—Acute.
*Base shape.*—Cordate.
*Degree of undulation.*—Weak.
*Length.*—Approximately 6.7 cm.
*Width.*—Approximately 8.0 cm.
*Diameter of petiole.*—Approximately 3.1 mm.
*Length of petiole.*—Approximately 7.4 cm.
*Color of upper surface.*—Moderate yellow green (Near R.H.S. 137C).
*Color of reverse surface.*—Moderate yellow green (Near R.H.S. 138C).
*Anthocyanin coloration of reverse surface.*—Present.
*Degree of anthocyanin coloration.*—Light.
*Pubescence of upper surface.*—Dense.
*Pubescence of reverse surface.*—Dense.
*Color of pubescence of reverse surface.*—White.
Flower cluster (gather of corymbs):
*Shape of flower cluster.*—Uneven.
*Diameter of flower cluster.*—Approximately 36 cm.
*Height of flower cluster.*—Approximately 18 cm.
Capitula:
*Transected shape of capitula.*—Flat.
*Diameter of capitula.*—Approximately 7.7 cm.
*Diameter of entire disc.*—Approximately 1.3 cm.
*Color of ray florets.*—Vivid violet (Near R.H.S. 89C).
*Marginal variegation.*—Absent.
*Color of disc florets.*—Deep violet (Near R.H.S. 93A).
*Ray floret length.*—Approximately 3.2 cm.
*Ray floret width.*—Approximately 0.8 cm.
*Shape of ray floret.*—Rectangular.
*Lengthwise warp of ray floret.*—Flat.
*Concavity of ray floret tip.*—Present.
*Shape of ray floret tip.*—Acute.
*Number of ray floret.*—Approximately 13–15.
*Number of disc floret.*—Approximately 135.
*Diameter of pedicel of the first capitulum.*—Approximately 1.0 mm.
*Length of pedicel of the first capitulum.*—Approximately 5.5 cm.
*Number of capitula per flower cluster.*—Approximately 65.
*Scent.*—Present.
Phyllaries:
*Length.*—Approximately 1.0 mm.
*Color.*—Very pale green (Near R.H.S. 130D).
*Anthocyanin coloration.*—Present.
Pistil:
*Color.*—Deep violet (Near R.H.S. 93A).
*Number.*—1.
*Type.*—Style branches truncate (i.e., the top of the style is separated into two and the shape of the top is truncated).
Stamen:
*Color.*—Deep violet (Near R.H.S. 93A).
*Type.*—5 anthers are connate, with separated filaments.
*Blooming period.*—Start at the beginning of December (cutting in July).

Hardiness:
*Cold.*—Good.
*Rain.*—Good.
*Heat.*—Good.
Resistance:
*Disease.*—Good.
*Insect.*—Good.

The botanical characteristics of similar variety 'Miss Yokohama', used as a comparison variety, are as follows.

Plant:
*Growth habit.*—Dwarf compact.
*Height.*—Approximately 19 cm.
Stem:
*Thickness.*—Approximately 5.4 mm.
*Color.*—Moderate yellow green (Near R.H.S. 139C).
*Anthocyanin coloration.*—Present.
*Degree of anthocyanin coloration.*—Medium.
*Branching.*—Fair.
*Pubescence.*—Dense.
*Internode length at the middle of main stem.*—Approximately 0.5 cm.
Leaf:
*Whole shape.*—Heart form with a swollen basal part, which is notched where the basal part of the leaf attaches to the petiole.
*Depth of concavity of leaf margin.*—Medium.
*Type of convexity.*—Acute.
*Size of wing (swollen basal part).*—Large.
*Apex shape.*—Obtuse.
*Base shape.*—Cordate.
*Degree of undulation.*—Weak.
*Length.*—Approximately 17.5 cm.
*Width.*—Approximately 13.0 cm.
*Diameter of petiole.*—Approximately 5.2 mm.
*Length of petiole.*—Approximately 7.7 cm.
*Color of upper surface.*—Moderate yellow green (Near R.H.S. 137C).
*Color of reverse surface.*—Moderate yellow green (Near R.H.S. 138C).
*Anthocyanin coloration of reverse surface.*—Present.
*Degree of anthocyanin coloration.*—Medium.
*Pubescence of upper surface.*—Dense.
*Pubescence of reverse surface.*—Dense.
*Color of pubescence of reverse surface.*—White.
Flower cluster (gathering of corymbs):
*Shape of flower cluster.*—Rounded.
*Diameter of flower cluster.*—Approximately 23 cm.
*Height of flower cluster.*—Approximately 17 cm.
Capitula:
*Transected shape of capitula.*—Flat.
*Diameter of capitula.*—Approximately 4.2 cm.
*Diameter of entire disc.*—Approximately 1.1 cm.
*Color of ray floret.*—Vivid violet (Near R.H.S. 96A).
*Marginal variegation.*—Present.
*Diameter of off color part.*—Approximately 2.5 cm.
*Border of marginal variegation.*—Fairy clear.
*Color of disc floret.*—Deep violet (Near R.H.S. 93A).
*Ray floret length.*—Approximately 1.6 cm.
*Ray floret width.*—Approximately 0.8 cm.
*Shape of ray floret.*—Generally rectangular.
*Lengthwise warp of ray floret.*—Convex.
*Concavity of ray floret tip.*—Present.
*Shape of ray floret tip.*—Rounded.
*Number of ray floret.*—Approximately 13.
*Number of disc floret.*—Approximately 86.
*Diameter of pedicel of the first capitulum.*—Approximately 1.7 mm.
*Length of pedicel of the first capitulum.*—Approximately 2.7 cm.
*Number of capitula per plant.*—Approximately 90.
*Scent.*—Present.
Phyllaries:
*Length.*—Approximately 1.2 mm.
*Color.*—Very pale green (Near R.H.S. 130D).
*Anthocyanin coloration.*—Absent.
Pistil:
*Color.*—Deep violet (Near R.H.S. 93A).
*Number.*—1.
*Type.*—Style branches truncate (i.e., the top of the style is separated into two and the shape of the top is truncated).
Stamen:
*Color.*—Deep violet (Near R.H.S. 93A).
*Type.*—5 anthers are connate, with separated filaments.
Blooming period — January (Sowing in August).
Hardiness:
*Cold.*—Good.
*Rain.*—Good.
*Heat.*—Good.
Resistance:
*Disease.*—Good.
*Insect.*—Good.

SUMMARY OF THE NEW VARIETY

'Sunsenerabu' is a dome-shaped plant with an approximate height of 39.5 cm in the blooming period. There is a branch from every node and branching is abundant, i.e., approximately 9 to 11 branches. The stem is approximately 4.9 mm in diameter with light pubescence.

The leaves are small, approximately 7.6 cm long and approximately 9.2 cm wide. The leaves are shaped in a serrated heart form with a swollen basal part, which is notched where the basal part of the blade attaches to the petiole. The leaf color is strong yellow green, with no anthocyanin coloration on the reverse side. Pubescence on upper side of leaf is sparse and pubescence on the reverse side is dense. The petiole is approximately 9.2 cm long and approximately 3.2 mm in diameter.

The new variety has large inflorescence clusters, which are high and flat in shape (i.e., the individual capitula forming the cluster are flat). An inflorescence cluster means a gathering of capitula in a plant. The capitulum is a single inflorescence with marginal variegation and has an obscure border. The capitulum has a flat transected shape (i.e., when the capitulum opens, ray florets are flat when viewed from the side). The capitulum is approximately 7.4 cm in diameter, while the entire disc is approximately 1.3 cm in diameter. The ray floret is approximately 3.0 cm long and approximately 0.8 cm wide. The color of the ray floret is light violet (near R.H.S. 91A), while the color of the disc florets are violet (near R.H.S. 90B). One capitulum has approximately 13 ray florets and approximately 149 disc florets. A ray floret has a pistil, but no stamen. A disc floret is tubular and has a pistil and a stamen formed by 5 connate anthers with separated filaments. There are approximately 180 capitula per plant. The length of the phyllary is approximately 2.0 mm. The phyllary is flat and has no anthocyanin coloration. The pedicel is approximately 3.5 cm long and approximately 1.3 mm in diameter. The capitula have some scent.

After cutting in July, the new variety 'Sunsenerabu' flowers at the end of the January in Omori-cho, Yokaichi-shi, Shiga-ken, Japan. The blooming continues from January to May, if under appropriate control. At a temperature of around 15° C., the individual bloom lasts two weeks. The inflorescence buds grow one after another from the axil. The inflorescence is not self-cleaning because the ray florets remain attached in a wilted and dry state as they fully mature.

The new variety has moderate cold and heat tolerance. The new variety does not die at temperatures of around 0° C., but when frost occurs the cells can necrose resulting in the death of the plant. Usually, *Senecio cruentus* has a tendency of slightly reduced growth in the hot session, whereas the new variety has no problem growing in the hot season.

The fertility of the new variety is low. Generally, *Senecio* plants have high fertility (i.e., bear many seeds per flower). In contrast, 'Sunsenerabu' bears no seed or very few seeds per capitulum. When no seed is formed, there is a part corresponding to a seed coat, which remains in an immature state, i.e., without embryo and endosperm.

The new variety, 'Sunsenerabu', differs from similar 'Sececio' varieties 'Sunsenebu' and 'Miss Yokohama' varieties and from the parental varieties *Senecio heritieri* (unnamed) and '8S-84e' in the following points.

1. 'Sunsenerabu' is taller than 'Miss Yokohama', *Senecio heritieri* (pollen parent) and '8S-84e'.
2. The capitulum of 'Sunsenerabu' has light violet ray florets, strong violet disc florets and obscure marginal variegation. 'Sunsenebu' has vivid violet ray florets, deep violet disc florets and no marginal variegation. 'Miss Yokohama' has vivid violet ray florets, vivid violet disc florets and no marginal variegation. The female parent '8S-84e' has white ray florets, white disc florets and no marginal variegation. The pollen parent *Senecio heritieri* (unnamed) has strong purple ray florets, strong reddish purple disc florets and white marginal part.
3. The petiole length of 'Sunsenerabu' is longer than that of 'Sunsenebu' or 'Miss Yokohama'.
4. 'Sunsenerabu' has less stem pubescence than that of 'Miss Yokohama'.
5. The blooming period of 'Sunsenerabu' is longer than that of 'Miss Yokohama'.
6. The fertility of 'Sunsenerabu' is lower than that of 'Miss Yokohama'.

The plant height and flower color are the most distinctive characteristics of this new variety, 'Sunsenerabu'.

DESCRIPTION OF THE NEW VARIETY

Figure 1:
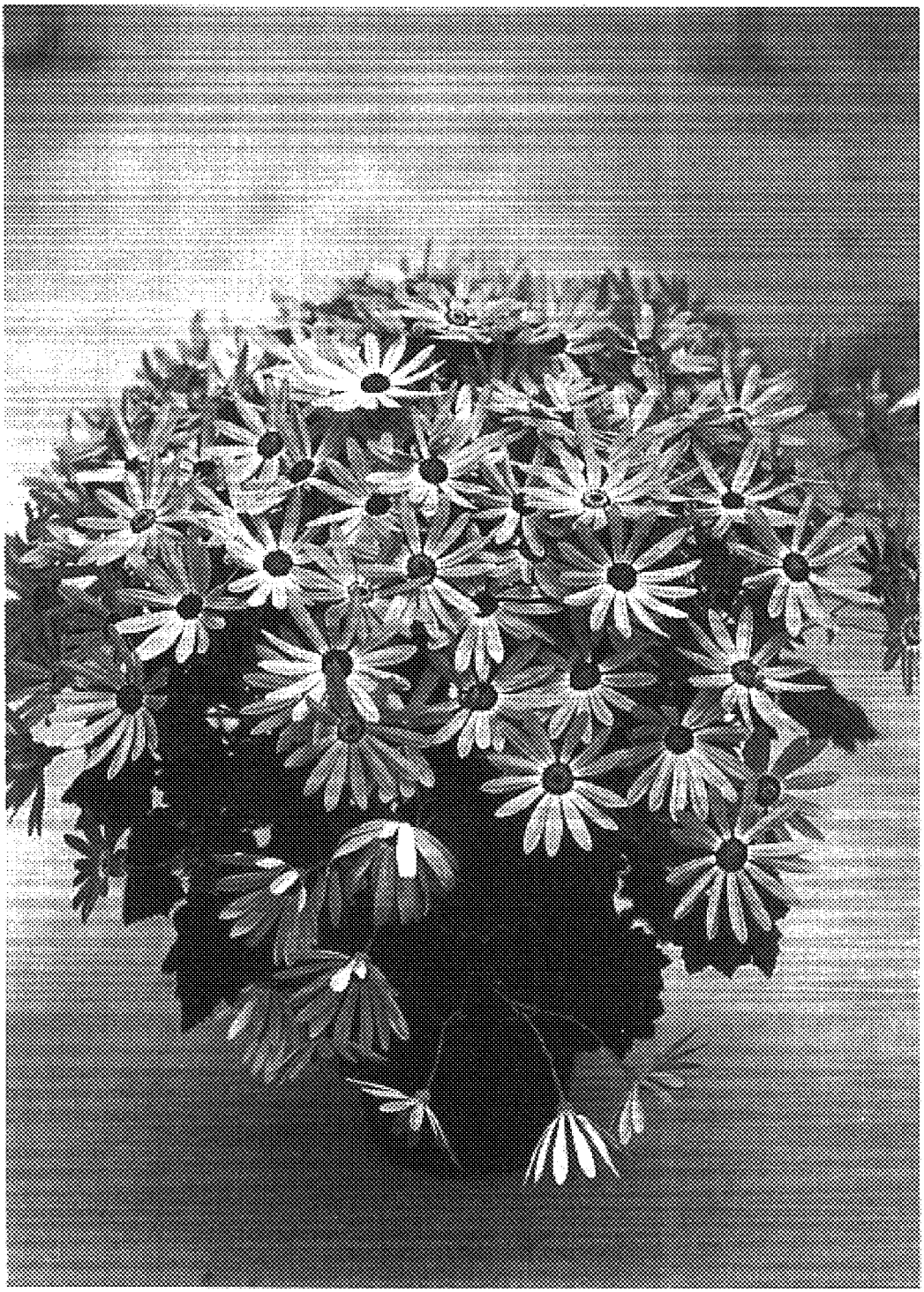
FIG. 1 is a photograph giving a partial view of the new variety of *Senecio* plant named 'Sunsenerabu' planted in a pot.
Figure 2:
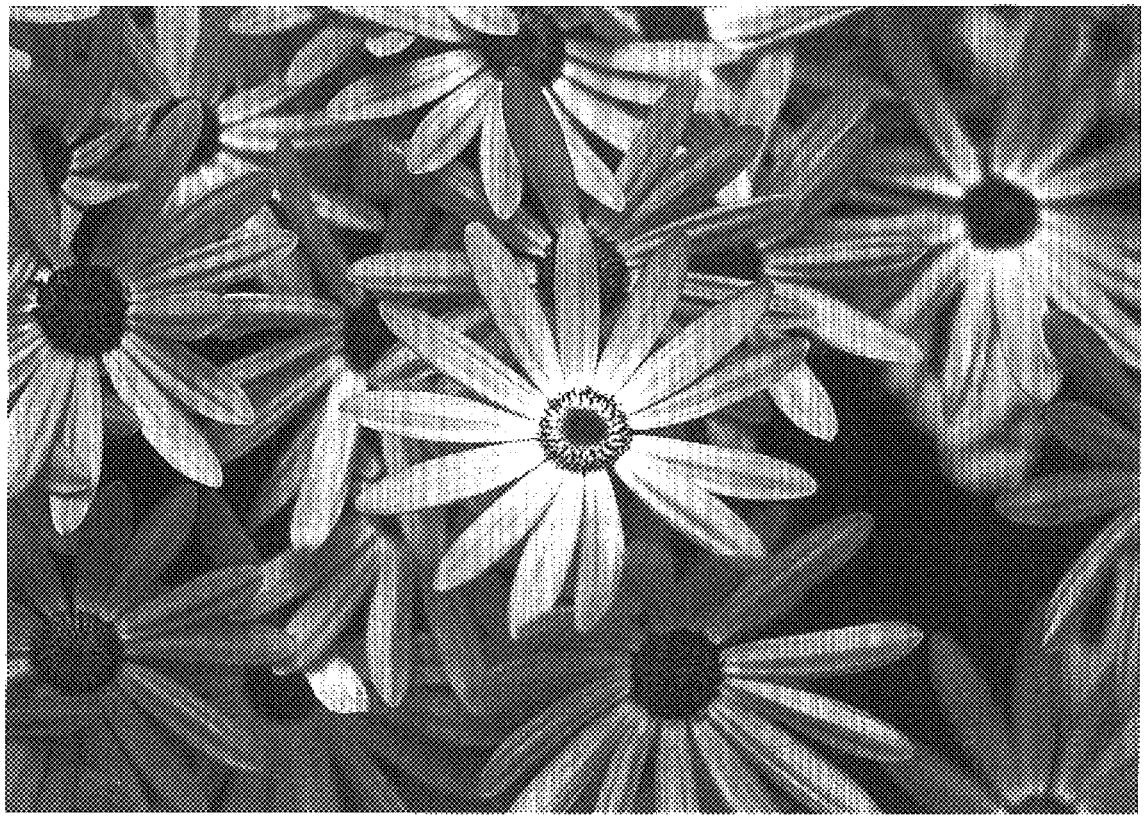
FIG. 2 is a photograph of capitula of the new variety of *Senecio* plant named 'Sunsenerabu'.

The botanical characteristics of the new and distinct variety of *Senecio* plant named 'Sunsenerabu' are set forth hereafter. The plants were observed during January 2002 in Yokaichi-shi, Shiga-ken, Japan, planted in 15 cm diameter pots, at an age of approximately 6 months.

Plant:
- *Growth habit.*—Semi-dwarf erect.
- *Height.*—Approximately 39.5 cm.
- *Spread.*—Approximately 45.0 cm.
- *Main stem length.*—Approximately 38.0 cm.
- *Lateral branches length.*—Approximately 20 cm.

Stem:
- *Thickness.*—Approximately 4.9 mm.
- *Color.*—Light yellow green (near R.H.S. 144D).
- *Anthocyanin coloration.*—Absent.
- *Branching.*—Abundant, i.e., approximately 9 to 11 branches.
- *Type of primary lateral shoot.*—Branch from every node.
- *Pubescence.*—Sparse.
- *Internode length at the middle of main stem.*—Approximately 2.1 cm.

Leaf:
- *Whole shape.*—Heart form with a swollen basal part, which is notched where the basal part of the blade attaches to the petiole.
- *Depth of concavity of leaf margin.*—The maximum depth of concavity measured from the average convexity peak height is approximately 5 mm.
- *Type of convexity.*—Acute.
- *Apex shape.*—Acute.
- *Base shape.*—Cordate.
- *Leaf margin.*—Palmately lobed, crenate and weakly undulated.
- *Length.*—Approximately 7.6 cm.
- *Width.*—Approximately 9.2 cm.
- *Diameter of petiole.*—Approximately 3.2 mm.
- *Length of petiole.*—Approximately 9.2 cm.
- *Color of petiole.*—Near R.H.S. 144D.
- *Color of upper surface.*—Strong yellow green (near R.H.S. 144A).
- *Color of reverse surface.*—Moderate yellow green (near R.H.S. 138C).
- *Anthocyanin coloration of reverse surface.*—Absent.
- *Pubescence of upper surface.*—Sparse.
- *Pubescence of reverse surface.*—Dense.
- *Color of pubescence of reverse surface.*—White.
- *Venation.*—Pattern Palmate; color near R.H.S. 136D.
- *Stipules.*—None.

Inflorescence cluster (gathering or corymbs):
- *Shape of inflorescence cluster.*—Flat.
- *Diameter of inflorescence cluster.*—Approximately 45 cm.
- *Height of inflorescence cluster.*—Approximately 17 cm.

Capitula:
- *Transected shape of capitula.*—Flat.
- *Diameter of capitula.*—Approximately 7.4 cm.
- *Diameter of entire disc capitula.*—Approximately 1.3 cm.

Disc floret:
- *Shape.*—Tubular, trumpet shape.
- *Color (both surfaces).*—Near R.H.S. N88B to 92C.
- *Length.*—Approximately 8.5 mm.
- *Diameter.*—Approximately 2.5 mm.
- *Margin.*—5 lobed, star shape.
- *Apex.*—Acute.
- *Base.*—Fused.
- *Number of disc florets per capitulum.*—Approximately 149.
- *Color of ray floret (upper surface).*—Near R.H.S. 91A.

*Color of ray floret* (*lower surface*).—Near R.H.S. 91D.
*Marginal variegation.*—Present.
*Size of marginal variegation.*—Approximately 1.7 cm.
*Border of marginal variegation.*—Obscure.
*Ray floret length.*—Approximately 3.0 cm.
*Ray floret width.*—Approximately 0.8 cm.
*Shape of ray floret.*—Rectangular.
*Lengthwise warp of ray floret.*—Flat.
*Concavity of ray floret tip.*—Present.
*Shape of ray floret tip.*—Acute.
*Number of ray florets.*—Approximately 13.
*Diameter of pedicel of the first capitulum.*—Approximately 1.3 mm.
*Length of pedicel of the first capitulum.*—Approximately 3.5 cm.
*Pedicel color.*—Near R.H.S. 144D.
*Number of capitula per plant.*—Approximately 180.
*Ray floret margin.*—Entire.
*Shape of ray floret base.*—Obtuse.
*Ray floret texture.*—Smooth, velvety.
*Scent.*—Present.

Phyllaries:
*Shape.*—Lanceolate.
*Apex.*—Acute.
*Margin.*—Entire.
*Base.*—Fused.
*Length.*—Approximately 2.0 mm.
*Width.*—Approximately 1.0 mm.
*Color* (*both surfaces*).—Near R.H.S. 143A.
*Number of phyllaries.*—Approximately 14.

Pistil:
*Color.*—Vivid purple (near R.H.S. 87A).
*Number.*—1 per ray floret and 1 per disc floret.
*Type.*—Style branches truncate (i.e., the top of the style is separated into two and the shape of the top is truncated).

Stamen:
*Color.*—Dark greenish yellow (near R.H.S. 152D).
*Type.*—Each disc floret has 5 connate anthers, with separated filaments.
*Amount of pollen.*—Scarce.
*Pollen color.*—Near R.H.S. 21A.
*Time to produce a plant.*—Approximately 6 months (cutting in July, inflorescences produced the following January in Japan).
*Blooming period.*—Starts at the end of January (cutting in July).
*Number of inflorescences per lateral stem.*—Approximately 5.
*Flowering time.*—From January to early May.

Bud.
*Hardiness.*—Susceptible to damage under 0° C.
*Diameter.*—Approximately 6 cm.
*Length.*—Approximately 4 cm.
*Shape.*—Globose.
*Surface.*—Pubescent.
*Color.*—Near R.H.S. 144D.
*Lastingness of an individual bloom on the plant.*—Approximately 10 days.

Hardiness:
*Cold.*—Good.
*Rain.*—Good.
*Heat.*—Good.

Resistance:
*Disease.*—Good.
*Insect.*—Good.

The new variety and *Senecio cruentus* have similar resistance to powdery mildew, leaf spot, aphid, whitefly, and thrips. The new variety, 'Sunsenerabu', is a tall plant and most suitable for flower potting.

This new and distinct variety of *Senecio* plant named 'Sunsenerabu' was asexually reproduced by cutting in Omori-cho, Yokaichi-shi, Shiga-ken, Japan and the homogeneity and stability thereof were confirmed.

It is claimed:

1. A new and distinct variety of *Senecio* plant named 'Sunsenerabu', substantially as herein illustrated and described.

* * * * *